United States Patent [19]
Ruddy et al.

[11] Patent Number: 5,503,723
[45] Date of Patent: Apr. 2, 1996

[54] ISOLATION OF ULTRA SMALL PARTICLES

[75] Inventors: Stephen B. Ruddy, Schwenksville; W. Mark Eickhoff, Dowingtown, both of Pa.

[73] Assignee: Eastman Kodak Company, Rochester, N.Y.

[21] Appl. No.: 385,531

[22] Filed: Feb. 8, 1995

[51] Int. Cl.$^6$ .................................................. B01D 57/02
[52] U.S. Cl. ........................ 204/450; 204/549; 209/128; 209/129; 209/130
[58] Field of Search ................................... 96/69, 70, 87; 95/59, 69, 70, 78, 79; 204/180.1, 299 R, 302; 209/127.1, 127.4, 129, 131, 133

[56] References Cited

U.S. PATENT DOCUMENTS

| | | | |
|---|---|---|---|
| 2,077,505 | 4/1937 | Woelflin | 204/1 |
| 3,162,592 | 12/1964 | Pohl | 204/186 |
| 3,509,035 | 4/1970 | Huebner | 204/299 |
| 3,630,882 | 12/1971 | Dilworth III | 204/299 |
| 3,790,461 | 2/1974 | Yeh | 204/180 |
| 3,873,432 | 3/1975 | Israel et al. | 204/180 G |
| 3,893,898 | 7/1975 | Candor | 204/180 R |
| 4,003,811 | 1/1977 | Kunkle | 204/180 R |
| 4,107,208 | 8/1978 | Schreiber et al. | 260/586 F |
| 4,141,809 | 2/1979 | Aitchison et al. | 204/180 R |
| 4,501,726 | 2/1985 | Schroder et al. | 424/1.1 |
| 4,540,602 | 9/1985 | Motoyama et al. | 427/213.31 |
| 4,569,739 | 2/1986 | Klinkowski | 204/180.1 |
| 4,713,249 | 12/1987 | Schroder | 424/488 |
| 4,725,442 | 2/1988 | Haynes | 424/490 |
| 4,737,268 | 4/1988 | Giddings | 209/12 |
| 4,826,689 | 5/1989 | Violanto et al. | 424/489 |
| 5,080,770 | 1/1992 | Culkin | 204/182.3 |
| 5,118,528 | 6/1992 | Fessi et al. | 427/213.36 |
| 5,131,994 | 7/1992 | Shmidt et al. | 204/180.1 |
| 5,133,908 | 7/1992 | Stainmesse et al. | 264/4.1 |
| 5,145,684 | 9/1992 | Liversidge et al. | 424/489 |
| 5,173,164 | 12/1992 | Egen et al. | 204/301 |
| 5,202,129 | 4/1993 | Samejima et al. | 424/489 |

FOREIGN PATENT DOCUMENTS 0602702  6/1994  European Pat. Off. ......... A61K 9/14

OTHER PUBLICATIONS

L. Lachman, H. Lieberman & J. Kanig, "The Theory and Practice of Industrial Pharmacy", 1970, Chptr. II, p. 45.

Gursoy, Eroglu, Ulutin, Tasyurek, Fessi, Puisieux & Devissaguet, "Evaluation of Indomethacin Nanocapsules for their Physical Stability and Inhibitory Activity on Inflammation and Platelet Aggregation", International Journal of Pharmaceutics, vol. 52, pp. 101, 108.

B. B. Van Orman, abstract 113, 199th ACS National Meeting, Apr. 22–27, 1990.

A. Eychmüller et al., Langmuir, 1990, 6, 1605–1608.

*Primary Examiner*—John Niebling
*Assistant Examiner*—Alex Noguerola
*Attorney, Agent, or Firm*—Carl F. Ruoff; Arthur H. Rosenstein

[57] ABSTRACT

The present invention is a method and apparatus for further reducing the size of nanoparticles. Nanoparticles are defined as having an effective average particle size of less than about 400 nm. The present invention separates the nanoparticles further using electric fields.

7 Claims, 2 Drawing Sheets

ISOLATION OF ULTRA SMALL PARTICLES

FIELD OF THE INVENTION

The present invention relates to drug particles and methods of their preparation. More particularly, the present invention discloses method and apparatus for further reducing the particle size distribution of nanoparticle dispersions.

BACKGROUND OF THE INVENTION

It is known that the rate of dissolution of a particulate therapeutic agent can increase with increasing surface area, i.e., decreasing particle size. Consequently, methods of making finely divided therapeutic agents have been studied and efforts have been made to control the size and size range of therapeutic agent particles in pharmaceutical compositions. For example, dry milling techniques have been used to reduce particle size and hence influence therapeutic agent absorption. However, in conventional dry milling, as discussed by Lachman, et al.. *The Theory and Practice of Industrial Pharmacy*, Chapter 2, "Milling", p, 45, (1986), the limit of fineness is reached in the region of 100 microns (100,000 nm) when material cakes on the milling chamber. Lachman. et al. note that wet grinding is beneficial in further reducing particle size, but that flocculation restricts the lower particle size limit to approximately 10 microns (10,000 nm). However, there tends to be a bias in the pharmaceutical art against wet milling due to concerns associated with contamination. Commercial airier milling techniques have provided particles ranging in average particle size from as low as about 1 to 50 µm (1,000–50,000 nm).

Other techniques for preparing pharmaceutical compositions include loading therapeutic agents into liposomes or polymers, e.g., during emulsion polymerization. However, such techniques have problems and limitations. For example, a lipid soluble therapeutic agent is often required in preparing suitable liposomes. Further, unacceptably large amounts of the liposome or polymer are often required to prepare unit therapeutic agent doses. Further still, techniques for preparing such pharmaceutical compositions tend to be complex. A principal technical difficulty encountered with emulsion polymerization is the removal of contaminants, such as unreacted monomer or initiator, which can be toxic, at the end of the manufacturing process.

U.S. Pat. No. 4,540,602 (Motoyama et al.) discloses a solid therapeutic agent pulverized in an aqueous solution of a water-soluble high molecular substance using a wet grinding machine. However, Motoyama et al. teach that as a result of such wet grinding, the therapeutic agent is formed into finely divided particles ranging from 0.5 µm (500 nm) or less to 5 µm (5,000 nm) in diameter.

EPO 275,796 describes the production of colloidally dispersible systems comprising a substance in the form of spherical particles smaller than 500 nm. However, the method involves a precipitation effected by mixing a solution of the substance and a miscible nonsolvent for the substance and results in the formation of noncrystalline nanoparticles. Furthermore, precipitation techniques for preparing particles tend to provide particles contaminated with solvents. Such solvents are often toxic and can be very difficult, if not impossible, to adequately remove to pharmaceutically acceptable levels to be practical.

U.S. Pat. No. 4,107,288 describes particles in the size range from 10 to 1,000 nm containing a biologically or pharmacodynamically active material. However, the particles comprise a crosslinked matrix of macromolecules having the active material supported on or incorporated into the matrix.

U.S. Pat. No. 4,725,442 (Haynes) describes water insoluble therapeutic agent materials solubilized in an organic liquid and incorporated in microencapsules of phospholipids. However, the toxic effects of solubilizing organic liquids is difficult to overcome. Other methods of formation of pharmaceutical therapeutic agent microencapsule include:

a) Micronizing a slightlysoluble therapeutic agent by subjecting a mixture of the therapeutic agent and a sugar or sugar alcohol to highspeed stirring comminution or impact comminution (EP 411,629A) together with suitable excipients or diluents. Such a method of encapsule formation does not lead to particle size as small as obtained by milling.

b) Polymerization of a monomer in the presence of the active therapeutic agent material and a surfactant can lead to smallparticle microencapsule (International Journal of Pharmaceutics, Vol. 52, pp. 101 108, 1989). This process, however, contains difficulttoremove contaminants such as toxic monomers. Complete removal of such monomers can be expensive in manufacturing scales.

c) Codispersion of a therapeutic agent or a pharmaceutical agent in water with droplets of carbohydrate polymer has been disclosed (U.S. Pat. No. 4,713,249 and WO-84/00294). The major disadvantage of the procedure is that in many cases, a solubilizing organic cosolvent is needed for the encapsulation procedure. Removal of traces of such harmful cosolvents can lead to expensive manufacturing processes.

It would be desirable to provide stable dispersible therapeutic agent particles in the submicron size range which can be readily prepared and which do not appreciably flocculate or agglomerate due to interparticle attractive forces and do not require the presence of a crosslinked matrix. Moreover, it would be highly desirable to provide pharmaceutical compositions having enhanced bioavailability.

SUMMARY OF THE INVENTION

The present invention is a method and apparatus for separating a nanoparticle dispersion. The apparatus includes an inlet for introducing the nanoparticle dispersion having a first particle size distribution. A first electrode extends longitudinally from the inlet and a second electrode spaced from the first electrode and parallel thereto also extends from the inlet. A voltage supply is coupled to the first and second electrodes. An outlet is positioned between an end of the first electrode and an end of the second electrode. The outlet is separated into two zones, the first zone is used for collecting a portion of the nanoparticle dispersion which has a second particle size distribution less than the first particle size distribution. The second zone collects a second portion of the nanoparticle dispersion which has a third particle size distribution greater than the first particle size distribution. The second portion can be recycled back into the apparatus or it can be discharged.

The method of the present invention refines a nanoparticle dispersion having a first particle size distribution. A nanoparticle dispersion is placed between a first electrode and a second electrode. An electric field is applied between the first electrode and the second electrode. A portion of the nanoparticle dispersion is withdrawn at a position between the first and second electrodes, the portion of the nanoparticle dispersion having a second particle size distribution less than the first particle size distribution.

An alternate method of the present invention refines a nanoparticle dispersion having a first particle size distribution. A nanoparticle dispersion is flowed laminarly between a first electrode and a second electrode. An electric field is applied between the first electrode and the second electrode. A portion of the nanoparticle dispersion is removed from an end at a is position between the first electrode and the second electrode, the portion of the nanoparticle dispersion having a particle size distribution less than the first particle size distribution.

In a preferred embodiment of the method described above, the nanoparticle dispersion includes a surface modifier capable of stabilizing the nanoparticles, It is preferred that this surface modifier has a positive or negative charge.

DESCRIPTION OF THE PREFERRED EMBODIMENT

Figure 1:
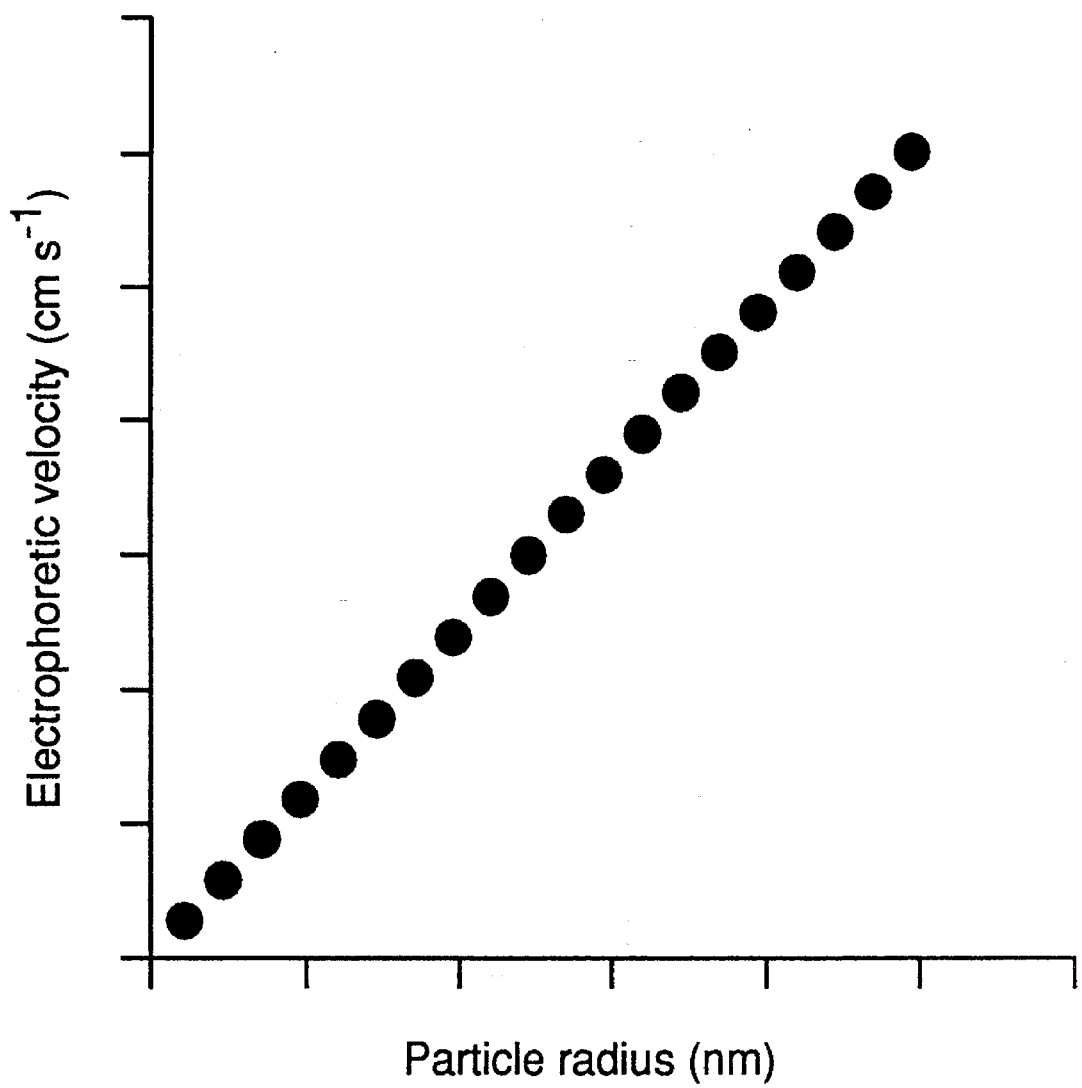
FIG. 1 illustrates the theoretical relationship between particle size and electrophoretic velocity.

The invention in U.S. Pat. No. 5,145,684 was based partly on the discovery that therapeutic agent particles having an extremely small effective average particle size can be prepared by wet milling in the presence of grinding media in conjunction with a surface modifier, and that such particles are stable and do not appreciably flocculate or agglomerate due to interparticle attractive forces and can be formulated into pharmaceutical compositions exhibiting unexpectedly high bioavailability.

While the invention is described herein primarily in connection with its preferred utility, i.e., with respect to nanoparticulate therapeutic or diagnostic agents for use in pharmaceutical compositions, it is also believed to be useful in other applications such as the formulation of particulate cosmetic compositions and the preparation of particulate dispersions for use in image and magnetic recording elements.

The particles comprise a therapeutic or diagnostic agent. (Therapeutic agents are sometimes referred to as drugs or pharmaceuticals. The diagnostic agent referred to is typically a contrast agent such as an x-ray contrast agent but can also be other diagnostic materials.) The therapeutic or diagnostic agent exists as a discrete, crystalline phase. The crystalline phase differs from a non-crystalline or amorphous phase which results from precipitation techniques, such as described in EPO 275,796.

The invention can be practiced with a wide variety of therapeutic or diagnostic agents. The therapeutic or diagnostic agent preferably is present in an essentially pure form. The therapeutic or diagnostic agent must be poorly soluble and dispersible in at least one liquid medium. By "poorly soluble" it is meant that the therapeutic or diagnostic agent has a solubility in the liquid dispersion medium of less than about 10 mg/ml, and preferably of less than about 1 mg/ml.

Suitable therapeutic or diagnostic agents can be selected from a variety of known classes of therapeutic or diagnostic agents including, for example, analgesics, anti-inflammatory agents, anthelmintics, antihythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac ionotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radiopharmaceuticals. sex hormones (including steroids), anti-allergic agents, stimulants and anoretics, sympathomimetics, thyroid agents, vasodilators and xanthines. Preferred therapeutic or diagnostic agents include those intended for oral administration and intravenous administration. A description of these classes of therapeutic agents and diagnostic agents and a listing of species within each class can be found in Martindale, The Extra Pharmacopoeia, Twenty-ninth Edition, The Pharmaceutical Press, London, 1989. The therapeutic or diagnostic agents are commercially available and/or can be prepared by techniques known in the art.

Representative illustrative species of therapeutic diagnostic agents include:

5a, 17a,-1'-(methylsulfonyl)-1'H-pregn- 20-yno[3,2-c]-pyrazol-17-ol (Danazol);

5,17,-1'-(methylsulfonyl)-1' H-pregn- 20-yno[3,2-c]-pyrazol-17-ol (Steroid A);

piposulfam;

piposulfan;

camptothecin; and ethyl-3,5-diacetoamido-2,4,6-triiodobenzoate

In particularly preferred embodiments, the therapeutic or diagnostic agent is asteroid such as danazol or Steroid A or an antiviral agent.

Surface modified nanoparticles comprising an NSAID, e.g., naproxen, demonstrate reduced gastric irritation and/or a more rapid onset of action following oral administration.

The NSAID preferably exists as a discrete, crystalline phase. The crystalline phase differs from an amorphous or non-crystalline phase which results from conventional solvent precipitation techniques, such as described in U.S. Pat. No. 4,826,689. The NSAID can be present in one or more suitable crystalline phases.

Suitable surface modifiers can preferably be selected from known organic and inorganic pharmaceutical excipients. Such excipients include various polymers, low molecular weight oligomers, natural products and surfactants. Preferred surface modifiers include nonionic and ionic surfactants.

Representative examples of surface modifiers include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthlate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the Handbook of Pharmaceutical Excipients, published jointly by the American Pharmaceutical Association and The Pharmaceutical Society of Great Britain, the Pharmaceutical Press, 1986.

Particularly preferred surface modifiers include polyvinylpyrrolidone, tyloxapol, polyoxamers such as Pluronic F68 and F108, which are block copolymers of ethylene oxide and propylene oxide, and polyxamines such as Tetronic 908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT, which is a dioctyl ester of sodium sulfosuccinic acid, available from American Cyanimid, Duponol P, which is a sodium lauryl sulfate, available from DuPont, Triton X-200, which is an alkyl aryl polyether sulfonate, available from Rohm and Haas, Tween 20 and Tween 80, which are polyoxyethylene sorbitan fatty acid esters, available from ICI Specialty Chemicals: Carbowax 3550 and 934, which are polyethylene glycols available from Union Carbide: Crodesta F-110, which is a mixture of sucrose stearate and sucrose distearate, available from Croda Inc., Crodesta SL-40, which is available from Croda, Inc., and SA90HCO, which is $C_{18}H_{37}$-$CH_2(CON(CH_3)CH_2(CHOH)_4CH_2OH)_2$. Surface modifiers which have been found to be particularly useful include Tetronic 908, the Tweens, Pluronic F-68 and polyvinylpyrrolidone. Other useful surface modifiers include:

decanoyl-N-methylglucamide;
n-decyl β-D-glucopyranoside:
n-decyl β-D-maltopyranoside:
n-dodecyl β-D-glucopyranoside;
n-dodecyl β-D-maltoside;
heptanoyl-N-methylglucamide:
n-heptyl-β-D-glucopyranoside;
n-heptyl β-D-thioglucoside; n-hexyl β-D-glucopyranoside;
nonanoyl-N-methylglucamide;
n-noyl β-D-glucopyranoside;
octanoyl-N-methylglucamide;
n-octyl-β-D-glucopyranoside;
octyl β-D-thioglucopyranoside; and the like.

Another useful surface modifier is tyloxapol (a nonionic liquid polymer of the alkyl aryl polyether alcohol type: also known as superinone or triton), This surface modifier is commercially available and/or can be prepared by techniques known in the art.

Another preferred surface modifier is p-isononylphenoxypoly(glycidol) also known as Olin-10G or Surfactant 10-G, is commercially available as 10G from Olin Chemicals. Stamford, Conn.

Preferred surface modifiers can be selected from known non-ionic surfactants, including the polyoxamines such as Tetronic 908 (also known as Polyxamines 908), which is a tetrafunctional block copolymer derived from sequential addition of propylene oxide and ethylene oxide to ethylenediamine, available from BASF, or Tetronic 1508 IT-1508), or a polymer of the alkyl aryl polyether alcohol type, such as tyloxapol.

The surface modifiers are commercially available and/or can be prepared by techniques known in the art. Two or more surface modifiers can be used in combination.

Tyloxapol (4-(1,1,3,3-tetramethylbutyl)-phenol polymer with ethylene oxide and formaldehyde) is a preferred surface modifier and is a nonionic liquid polymet of the alkyl aryl polyether alcohol type. Tyloxapol, also known as "Superinone", is disclosed as useful as a nonionic surface active agent in a lung surfactant composition in U.S. Pat. No. 4,826,821 and as a stabilizing agent for 2-dimethylaminoethyl 4-n-butylaminobenzoate in U.S. Pat. No. 3,272,700.

Tyloxapol may be associated with the nanoparticles and may function as a surface modifier, as a stabilizer, and/or as a dispersant. Alternatively, the tyloxapol may serve other purposes. Tyloxapol may serve all three functions. The tyloxapol may serve as a stabilizer and/or a dispersant, whereas another compound acts as a surface modifier.

Particularly preferred auxiliary surface modifiers are those which impart resistance to particle aggregation during sterilization and include dioctylsulfosuccinate (DOSS), polyethylene glycol, glycerol, sodium dodecyl sulfate dodecyl trimethyl ammonium bromide and a charged phospholipid such as dimyristoyl phophatidyl glycerol. The surface modifiers are commercially available and/or can be prepared by techniques known in the art. Two or more surface modifiers can be used in combination.

As used herein, particle size refers to a number average particle size as measured by conventional particle size measuring techniques well known to those skilled in the art, such as sedimentation field flow fractionation, photon correlation spectroscopy, or disk centrifugation. When photon correlation spectroscopy (PCS) is used as the method of particle sizing the average particle diameter is the Z-average particle diameter known to those skilled in the art. By "an effective average particle size of less than about 400 nm" it is meant that at least 90% of the particles have a weight average particle size of less than about 400 nm when measured by the above-noted techniques. In preferred embodiments, the effective average particle size is less than about 300 nm and more preferably less than about 250 nm. In some embodiments, an effective average particle size of less than about 100 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

Although nanoparticles have shown great effectiveness, it is apparent that further reductions in size of a nanoparticulate dispersion would increase effectiveness of the nanoparticles in essentially all applications. The present invention provides such a method and apparatus for further reducing nanoparticulate size distribution. The following description provides a theoretical basis for the present invention.

The movement of a particle i in an electric field may be described by the following equation:

$$v_i = \left[ \frac{D_i z_i F}{RT} \right] \frac{d\psi}{dx} \qquad (1)$$

where $v_i$ is the velocity of i, $D_i$ is the diffusion coefficient of i, $z_i$ is the surface charge of i, F is Faraday's constant, R is the Gas constant, T is the absolute temperature and $\Psi$ is the electrical potential (i.e.. the voltage drop) across the electrodes separated by distance x. The diffusion coefficient of a particle may be measured by several techniques (for example, low-angle laser light scattering) or may be estimated by means of the stokes-Einstein relationship:

$$D_i = \frac{kT}{6\pi\eta r_i} \qquad (2)$$

where k is the Boltzmann constant, η is the viscosity of the medium and $r_i$ is the radius of i. The surface charge $z_i$ may be obtained experimentally from the zeta potential of the particle or may be estimated, alternatively, by knowledge of the surface charge density $\rho_i$ at the particle surface:

$$z_i = 4\pi r_i^2 \rho_i \qquad (3)$$

Accordingly, by combining terms, the electrophoretic velocity of a particle in an externally applied electric field may be obtained as a function of its radius:

$$v_i = \frac{2}{3}\left[\frac{kr_i\rho_i F}{\eta R}\right]\frac{d\psi}{dx} \qquad (4)$$

FIG. 1 illustrates the theoretical relationship between particle size and electrophoretic velocity for nanoparticles possessing a uniform surface charge density under the influence of a nonuniform electric field, (i.e. an electric potential gradient). As predicted by Eq. (4), particle velocity is shown to be directly proportional particle size.

Equation 4 demonstrates the feasibility of isolating ultrasmall populations of surface-stabilized nanocrystals secondary to eletrophoretic separation, the efficiency of which may be controlled by the interelectrode distance, the magnitude of the electrical potential difference across the electrodes and the duration of the applied current.

The preceding model is based upon the following assumptions:
1. hydrodynamic effects are negligible
2. electrophoretic velocity>>diffusional velocity
3. particles assume a spherical geometry
4. packing density of surfactant molecules at the particle surface is independent of particle size (i.e., uniform) throughout the range of particles discussed herein.

In order to test the above theory regarding the isolation of the nanoparticulate dispersion, the following experiment was run. A polydisperse polystyrene nanoparticle dispersion containing approximately 0.25% solids was placed in a shallow plastic trough. Electrodes were then emersed in the nanoparticle dispersion separated by approximately 5 cm. An electrical potential difference was then initiated across the electrodes for a period of 1 hour, during which time a moving particle front was observed. At the end of 1 hour, 10-ml aliquots of dispersion were removed at 6 different locations along the anode-cathode axis. The aliquots were evaluated for particle size using the Microtrac UPA.

The results of the above described example are shown in Table 1.

TABLE 1

| Sample | Mean Particle Size (nm) | 10th Percentile (nm) | 90th Percentile (nm) | Calc. Specific Surface |
|---|---|---|---|---|
| anode (+++) | 220 | 151 | 387 | 29.3 |
| ++ | 215 | 117 | 337 | 31.5 |
| + | 210 | 103 | 349 | 33.4 |
| − | 200 | 85 | 290 | 36.0 |
| −− | 193 | 63 | 313 | 41.3 |
| cathode (−−−) | 220 | 131 | 724 | 33.2 |
| Mother dispersion | 216 | 129 | 614 | 31.8 |

As can be seen from Table 1, aliquots of the mother dispersion can be obtained which have a mean particle size less than the particle size of the mother dispersion. It should be noted that in these experiments, the mother dispersion was introduced near the cathode. Due to the experimental configuration; the results at the cathode are not as reliable as samples taken at other locations between the cathode and the anode.

Separations can be achieved more rapidly with the present invention for particles which possess a greater zeta potential. Accordingly, an experiment was run with a surfactant, a polysulfated tyloxapol, which yields zeta potential in excess of −70 mV. Described in the next example are the results of this experiment.

Strongly charged particles were produced by milling danazol in the presence of a polysulfonated tyloxapol and subjected to an electric field as described previously. After 1 hour, 10 ml aliquots of danazol dispersion were obtained from different locations along the anode/cathode axis, after which particle sizing was performed on the Microtrac UPA. The results are shown in Table 2.

TABLE 2

| Sample | Mean Particle Size (nm) | 10th Percentile (nm) | 50th Percentile (nm) | Calc. Specific Surface |
|---|---|---|---|---|
| Mother dispersion | 1054 | 234 | 468 | 12.8 |
| Anode (+++) | 642 | 228 | 688 | 13.4 |
| ++ | 539 | 199 | 278 | 20.1 |
| + | 380 | 180 | 243 | 24.1 |
| − | 352 | 207 | 258 | 22.7 |
| −− | too dilute | too dilute | too dilute | too dilute |
| cathode (−−−) | too dilute | too dilute | too dilute | too dilute |

As shown in Table 2, the data demonstrate threefold reduction in mean particle size distribution combined with a doubling of the calculated specific surface based upon a 1 hour separation at 30 volts. As such, the results provide additional evidence that electric current may be used to isolate sub-populations of nanoparticulate disperions.

Figure 2:
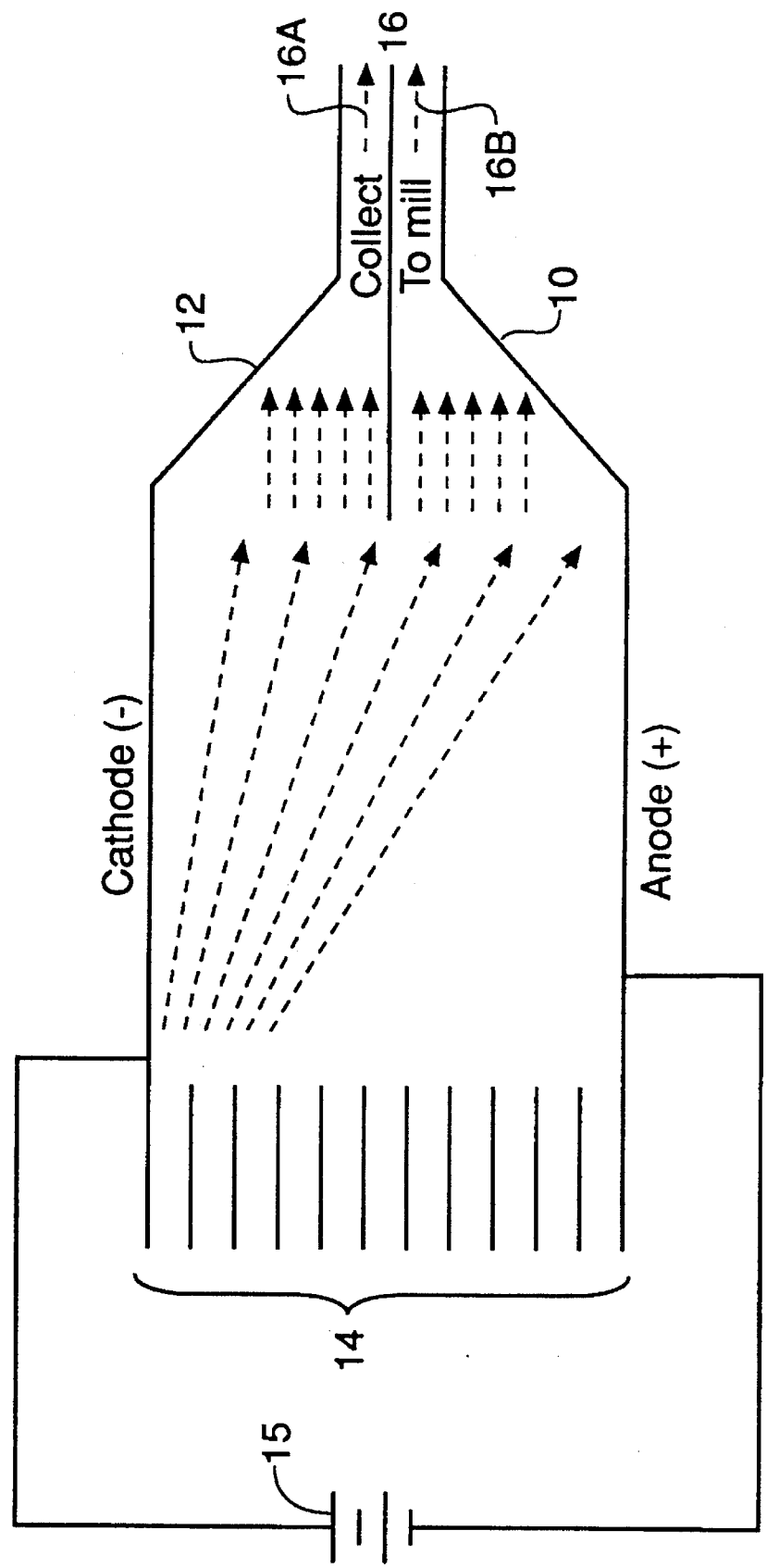
FIG. 2 is a schematic diagram of the apparatus of the present invention.

FIG. 2 shows an apparatus that can be used to continuously separate a dispersion of nanoparticles. As shown in FIG. 2, an anode 10 and cathode 12 are spaced apart and parallel to each other. The inlet 14 runs between the anode 10 and the cathode 12 and is used to introduce the nanoparticle dispersion. The voltage supply 15 is coupled to the anode 10 and the cathode 12 for providing an electric field between them. At the inlet, the nanoparticle dispersion is introduced in a laminar flow manner and subjected to the electric field. The nanoparticle dispersion is intoduced in the laminar flow regime to reduce eddies and other mixing (hydrodynamic) effects. Depending upon the nanoparticles in the nanoparticle dispersion, the larger particles will either be attracted to the anode or the cathode. This can be determined experimentally for each nanoparticle dispersion. As the nanoparticle dispersion moves through the chamber between the anode and the cathode, a separation is effected and a portion of the nanoparticle dispersion is collected which has a nanoparticle size distribution less than the nanoparticle size distribution of the dispersion introduced. This portion is collected at the outlet 16 in zone 16A. At the outlet 16, a second fraction is also collected at zone 16B which has a particle size distribution greater than the original particle size distribution. In the present example which illustrates the separation of negatively charge particles, the arrows in the chamber show the movement of the larger nanoparticles as they are attracted to the anode. This fraction can either be recycled or sent to a mill for further size reduction.

The invention has been described in detail with particular reference to preferred embodiments thereof, but it will be understood that the variations and modifications can be affected within the scope and spirit of the invention as defined by the following claims.

What is claimed is:

1. A method of refining a nanoparticle dispersion having a first particle size distribution comprising:

placing the nanoparticle dispersion between a first electrode and a second electrode;

applying an electric field between the first electrode and the second electrode;

removing a portion of the nanoparticle dispersion at a position between the first electrode and the second electrode, this portion of the nanoparticle dispersion having a second particle size distribution less than the first particle distribution;

wherein the nanoparticle dispersion consists essentially of particles of a poorly soluble crystalline therapeutic or diagnostic agent, wherein 99% of the particles have a particle size of less than 400 nm, and wherein the particles have associated with the surface thereof a surface modifier which is capable of stabilizing the nanoparticles.

2. The method according to claim 1 wherein the surface modifier has a positive or negative charge.

3. The method according to claim 1 wherein the surface modifier comprises polysulfated tyloxapol.

4. A method of refining a nanoparticle dispersion having a first particle size distribution comprising:

laminarly flowing the nanoparticle dispersion between a first electrode and a second electrode;

applying an electric field between the first electrode and the second electrode;

removing a portion of the nanoparticle dispersion from a position between the first electrode and the second electrode, this portion of the nanoparticle dispersion having a second particle size distribution less than the first particle distribution;

wherein the nanoparticle dispersion consists essentially of particles of a poorly soluble crystalline therapeutic or diagnostic agent, wherein 99% of the particles have a particle size of less than 400 nm, and wherein the particles have associated with the surface thereof a surface modifier which is capable of stabilizing the nanoparticles.

5. The method according to claim 4 further comprising:

removing a second portion of the nanoparticle dispersion from a position between the first electrode and the second electrode, the second portion of the nanoparticle dispersion having a third particle size distribution greater than the first particle distribution.

6. The method according to claim 4 wherein the surface modifier has a positive or negative charge.

7. The method according to claim 4 wherein the surface modifier comprises polysulfated tyloxapol.

* * * * *